(12) United States Patent
Wu (10) Patent No.: US 11,710,129 B2
(45) Date of Patent: Jul. 25, 2023

(54) BLOCKCHAIN-BASED METHOD AND APPARATUS FOR MANAGING BIOLOGICAL ASSET OBJECT

(71) Applicant: Alipay (Hangzhou) Information Technology Co., Ltd., Zhejiang (CN)

(72) Inventor: Yingqiang Wu, Zhejiang (CN)

(73) Assignee: Alipay (Hangzhou) Information Technology Co., Ltd., Hangzhou (CN)

( * ) Notice: Subject to any disclaimer, the term of this patent is extended or adjusted under 35 U.S.C. 154(b) by 0 days.

(21) Appl. No.: 17/353,525

(22) Filed: Jun. 21, 2021

(65) Prior Publication Data
US 2022/0036366 A1    Feb. 3, 2022

(30) Foreign Application Priority Data

Jul. 31, 2020   (CN) .......................... 202010757521.7

(51) Int. Cl.
| | |
|---|---|
| G06Q 40/00 | (2012.01) |
| G06Q 20/40 | (2012.01) |
| G06Q 20/38 | (2012.01) |
| H04L 9/32 | (2006.01) |
| H04L 9/00 | (2022.01) |

(52) U.S. Cl.
CPC ... *G06Q 20/40145* (2013.01); *G06Q 20/3825* (2013.01); *G06Q 20/38215* (2013.01); *H04L 9/3247* (2013.01); *H04L 9/50* (2022.05); *H04L 2209/56* (2013.01)

(58) Field of Classification Search
CPC .............................. G06Q 40/08; H04L 9/0643
See application file for complete search history.

(56) References Cited

U.S. PATENT DOCUMENTS

| | | | |
|---|---|---|---|
| 10,708,042 B1 * | 7/2020 | Rubenstein | ........... H04L 9/0643 |
| 2019/0251078 A1 | 8/2019 | Yan | |
| 2020/0159720 A1 | 5/2020 | Leong et al. | |
| 2020/0160460 A1 | 5/2020 | Fricke et al. | |

FOREIGN PATENT DOCUMENTS

| | | |
|---|---|---|
| CN | 108416675 A | 8/2018 |
| CN | 111199052 A | 5/2020 |
| EP | 3660855 A1 | 6/2020 |

* cited by examiner

*Primary Examiner* — Ojo O Oyebisi
(74) *Attorney, Agent, or Firm* — Seed IP Law Group LLP (57) ABSTRACT

The present specification provides a blockchain-based method and apparatus for managing a biological asset object. The method is performed by a node device in a blockchain network, a smart contract for managing a biological asset object is deployed in the blockchain, and processing logic corresponding to contract code of the smart contract includes biological asset object creation logic, the method including: obtaining an asset object creation transaction generated by a client, where the asset object creation transaction includes identification information of a target organism; and invoking the smart contract, executing the biological asset object creation logic, and creating a target biological asset object corresponding to the target organism based on the identification information of the target organism.

20 Claims, 5 Drawing Sheets

BLOCKCHAIN-BASED METHOD AND APPARATUS FOR MANAGING BIOLOGICAL ASSET OBJECT

BACKGROUND

Technical Field

One or more implementations of the present specification relate to the field of blockchain technologies, and in particular, to a blockchain-based method and apparatus for managing a biological asset object.

Description of the Related Art

A blockchain technology, also referred to as a distributed ledger technology, is an emerging technology that several computing devices jointly participate in "accounting" to maintain a complete distributed database. The blockchain technology is characterized by decentralization, openness, and transparency, and also, in the blockchain technology, each computing device can participate in database recording, and data can be synchronized rapidly between the computing devices. Therefore, the blockchain technology has been widely applied to many fields.

With the promotion and support for the agricultural financial development, the fields of logistics, cold chain and finance also provide more support for agriculture and animal husbandry. In addition to the consumption attribute, organisms with high economic value such as cattle, sheep, and horses also bring with them the financial attribute. How to digitalize biological assets effectively and reliably through a technical means has become a problem in the agricultural financial development.

BRIEF SUMMARY

One or more implementations of the present specification provide a blockchain-based method for managing a biological asset object. The method is performed by a node device in a blockchain network, a smart contract for managing a biological asset object is deployed in the blockchain, processing logic corresponding to contract code of the smart contract includes biological asset object creation logic, and the method includes: obtaining an asset object creation transaction generated by a client, the asset object creation transaction including identification information of a target organism; and invoking the smart contract, executing the biological asset object creation logic, and creating a target biological asset object corresponding to the target organism based on the identification information of the target organism.

In an illustrative implementation, the target biological asset object includes a unique identifier generated based on the identification information of the target organism.

In an illustrative implementation, the asset object creation transaction further includes an account identifier of a user who holds the biological asset object, and the executing the biological asset object creation logic further includes: storing the target biological asset object in a blockchain user account corresponding to the user account identifier.

In an illustrative implementation, the identification information of the target organism includes one or more of identity attribute information collected from sensing hardware mounted on the target organism or biological characteristic information of the target organism collected from the target organism.

In an illustrative implementation, the identity attribute information includes one or more of an identity number, a biological species, a place of origin, a breeding ground, and birth date information.

In an illustrative implementation, the biological characteristic information includes iris characteristic information or genetic material characteristic information.

Correspondingly, the present application further provides a blockchain-based apparatus for managing a biological asset object. The apparatus is applied to a node device in a blockchain network, a smart contract for managing a biological asset object is deployed in the blockchain, processing logic corresponding to contract code of the smart contract includes biological asset object creation logic, and the apparatus includes: an acquisition unit, configured to obtain an asset object creation transaction generated by a client, the asset object creation transaction including identification information of a target organism; and an execution unit, configured to invoke the smart contract, execute the biological asset object creation logic, and create a target biological asset object corresponding to the target organism based on the identification information of the target organism.

In an illustrative implementation, the target biological asset object includes a unique identifier generated based on the identification information of the target organism.

In an illustrative implementation, the asset object creation transaction further includes an account identifier of a blockchain user who holds the biological asset object, and the executing the biological asset object creation logic further includes: storing the target biological asset object in a blockchain user account corresponding to the account identifier.

In an illustrative implementation, the identification information of the target organism includes one or more of identity attribute information collected from sensing hardware mounted on the target organism or biological characteristic information of the target organism collected from the target organism.

In an illustrative implementation, the identity attribute information includes one or more of an identity number, a biological species, a place of origin, a breeding ground, and birth date information.

In an illustrative implementation, the biological characteristic information includes iris characteristic information or genetic material characteristic information.

Correspondingly, the present specification further provides a computer device, including a storage and a processor. The storage stores a computer program that can be run by the processor, and when running the computer program, the processor performs the blockchain-based method for managing a biological asset object that is performed by the node device in the above implementations.

According to the blockchain-based method and apparatus for managing a biological asset object and the computer device provided in the plurality of implementations of the present specification, through a smart contract technology, the target biological asset object corresponding to the target organism is created in the blockchain, so that an asset of the target organism is digitalized, and the target biological asset object can be managed in the blockchain. In addition, the target biological asset object created in the blockchain is generated based on the identification information of the target organism, and a blockchain-based tamper-resistant mechanism effectively prevents malicious tampering of information about the biological asset object in the blockchain.

DETAILED DESCRIPTION

Example implementations are described in detail herein, and examples of the example implementations are presented in the accompanying drawings. When the following description relates to the accompanying drawings, unless specified otherwise, the same numbers in different accompanying drawings represent same or similar elements.

Implementations described below do not represent all implementations consistent with one or more implementations of the present specification. On the contrary, the implementations are only examples of apparatuses and methods that are described in the appended claims in detail and consistent with some aspects of one or more implementations of the present specification.

It should be noted that in other implementations, steps of a corresponding method are not necessarily performed according to the sequence shown and described in the present specification. In some other implementations, the method can include more or less steps than those described in the present specification. In addition, a single step described in the present specification may be divided into a plurality of steps in other implementations for description, and a plurality of steps described in the present specification may also be combined into a single step for description in other implementations.

With the promotion and support of government agencies for the agricultural financial development, the fields of logistics, cold chain and finance also provide more support for agriculture and animal husbandry. In addition to the consumption attribute, organisms with high economic value such as cattle, sheep, and horses also bring with them the financial attribute. How to digitalize biological assets effectively and reliably through a technical means and manage the biological assets using digital information has become a problem in the agricultural financial development.

In view of the above problems, one or more implementations of the present specification provide a blockchain-based method for managing a biological asset object, to digitalize biological assets through a blockchain technology.

The blockchain or blockchain network described in the one or more implementations of the present specification can be a peer-to-peer (P2P) network system with a distributed data storage structure that is implemented by node devices through a consensus mechanism. Ledger data in the blockchain is distributed in "blocks" connected in time. A current block can include a data digest of a previous block, and data of all or some of the nodes is backed up based on different specific consensus mechanisms (for example, proof of work (POW), proof of stake (POS), delegated proof of stake (DPOS), or practical byzantine fault tolerance (PBFT)).

Real data generated in the physical world can be formed into a standard transaction format supported by the blockchain, and then published in the blockchain. Node devices in the blockchain perform consensus processing on the received transaction. After a consensus is reached, a node device serving as a mining node in the blockchain packs the transaction into a block and persistently stores the transaction in the blockchain.

Regardless of which consensus algorithm is used in the blockchain, the mining node can pack the received transaction to generate the latest block, and send the generated latest block to another node device for consensus verification. If another node device detects no problem after receiving the latest block, the other node device can append the latest block to the end of the blockchain, to complete an accounting process in the blockchain. When performing verification on a new block sent by the mining node, the other node can also execute a transaction included in the block.

It should be noted that each time the latest block is generated in the blockchain, corresponding states of transactions executed in the blockchain change accordingly after the transactions in the latest block are executed. For example, in a blockchain constructed by using an account model, an account state of an external account or a smart contract account usually also changes accordingly as transactions are executed.

For example, after a transfer transaction in a block is executed, balances of payer and payee accounts associated with the transfer transaction (i.e., field values of BALANCE fields of these accounts) usually change accordingly.

For another example, "smart contract invocation transaction" in a block is used to invoke a smart contract deployed in a blockchain. The smart contract is invoked in an Ethereum virtual machine (EVM) corresponding to a node device, to execute the "smart contract invocation transaction," and a data state corresponding to the smart contract invocation transaction is updated based on an execution result.

In practice, a smart contract can be provided in all of a public blockchain, a private blockchain, and a consortium blockchain. A smart contract in a blockchain is a contract that can be triggered by a transaction in the blockchain. The smart contract can be defined in the form of code.

Taking Ethereum as an example, users can create and invoke some complex logic in an Ethereum network. As a programmable blockchain, the core of Ethereum is an EVM, and each Ethereum node can run the EVM. The EVM is a Turing-complete virtual machine, through which various types of complex logic can be implemented. A smart contract published and invoked by a user in Ethereum can be run in the EVM. Actually, virtual machine code (virtual machine byte code, referred to as "byte code" below) is directly run in the EVM, and therefore, a smart contract deployed in a blockchain can be byte code.

Figure 1:
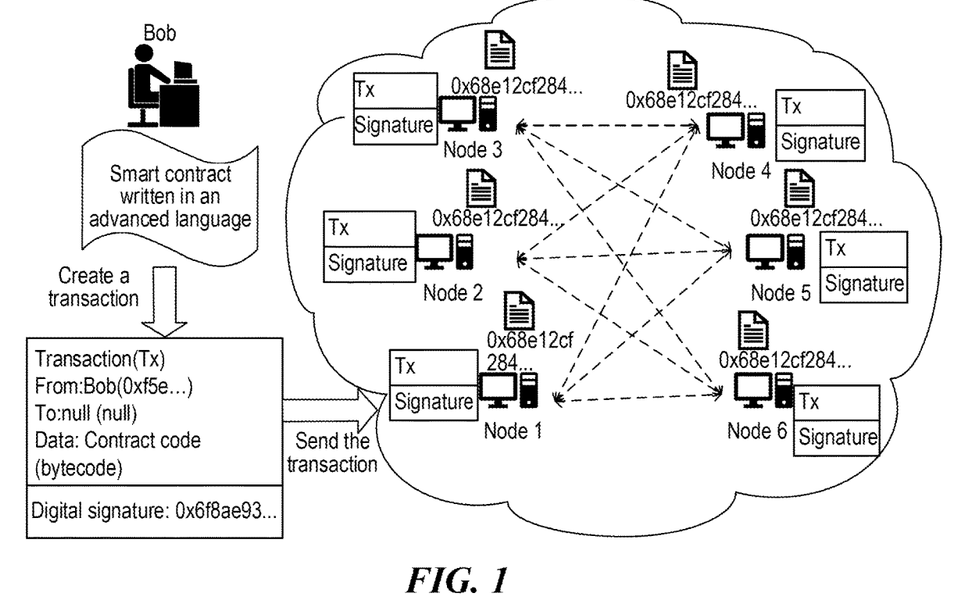
FIG. 1 is a schematic diagram illustrating creation of a smart contract according to an example implementation.

As shown in FIG. 1, after user "Bob" sends a transaction including information about creating a smart contract to the Ethereum network, each node can execute the transaction in the EVM. In FIG. 1, a FROM field of the transaction is used to record an address of an account that initiates creation of the smart contract, contract code stored in a field value of a DATA field of the transaction can be byte code, and a field value of a TO field of the transaction is a null account. After nodes reach a consensus by using a consensus mechanism, the smart contract is successfully created, and then a user can invoke the smart contract.

After the smart contract is created, a contract account corresponding to the smart contract appears in the blockchain and has a specified address. For example, "0x68e12cf284 . . . " in each node in FIG. 1 represents the address of the contract account created, and contract code and account storage will be stored in account storage of the contract account. Behavior of the smart contract is controlled by the contract code, and a contract state is stored in the account storage of the smart contract. In other words, a virtual account including contract code and account storage is generated in the blockchain by using the smart contract.

As mentioned above, a DATA field of a transaction including creating a smart contract can store byte code of the smart contract. The byte code includes a series of bytes. Each byte can identify one operation. Considering development efficiency, readability, etc., developers may not write byte code directly, but choose an advanced language to write smart contract code. For example, advanced languages can be Solidity, Serpent, and LLL. Smart contract code written in an advanced language can be compiled by using a compiler, to generate byte code that can be deployed in a blockchain.

Taking the Solidity language as an example, contract code written in the Solidity language is similar to class in an object-oriented programming language. A plurality of members can be stated in a contract, including a state variable, a function, a function modifier, an event, etc. The state variable is a value that is permanently stored in an ACCOUNT STORAGE field of a smart contract and is used to store a contract state.

Figure 2:
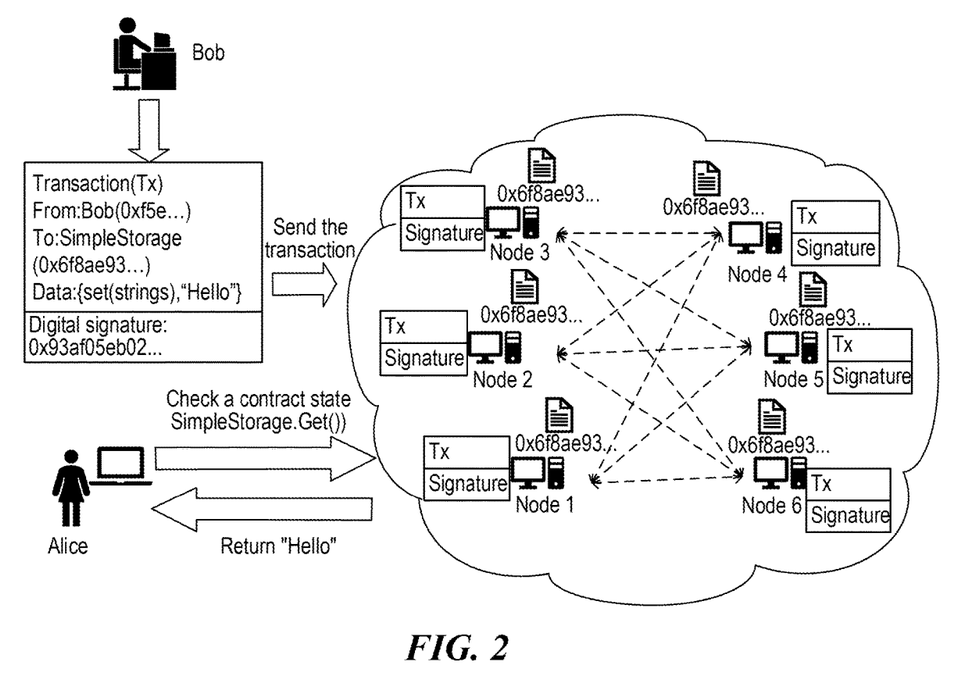
FIG. 2 is a schematic diagram illustrating invocation of a smart contract according to an example implementation.

As shown in FIG. 2, still using Ethereum as an example, after user "Bob" sends a transaction including information about invoking a smart contract to an Ethereum network, each node can execute the transaction in the EVM. In FIG. 2, a FROM field of the transaction is used to record an address of an account that initiates invocation of the smart contract, a TO field is used to record an address of the invoked smart contract, and a DATA field of the transaction is used to record a method and a parameter for invoking the smart contract. After the smart contract is invoked, an account state of the contract account can change. Subsequently, a client can view the account state of the contract account by using a connected blockchain node.

A smart contract can be executed independently on each node in a blockchain network in a specified way, and all execution records and data are stored in the blockchain. Therefore, after such a transaction is executed, transaction vouchers that cannot be tampered with and will not be lost are stored in the blockchain.

An execution result of the smart contract can be stored in a Merkle Patricia tree (MPT) receipt tree in the form of a transaction execution log, or can be stored in a storage tree of the smart contract in the form of a key-value pair.

Figure 3:
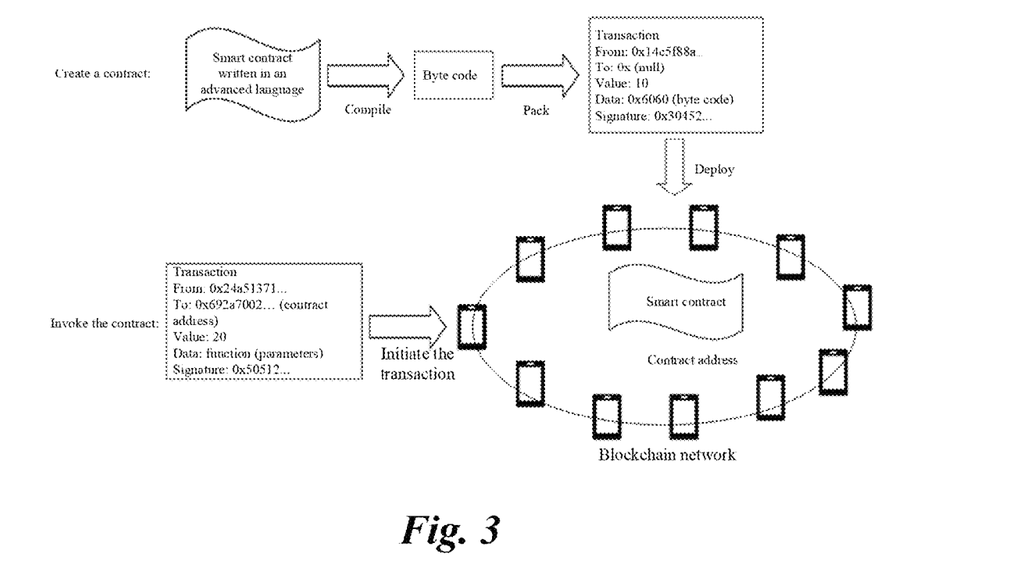
FIG. 3 is a schematic diagram illustrating creation and invocation of a smart contract according to an example implementation.

FIG. 3 is a schematic diagram illustrating creation and invocation of a smart contract. To create a smart contract in Ethereum, processes such as writing a smart contract, generating byte code, and deploying the byte code in a blockchain are needed. Invoking a smart contract in Ethereum is initiating a transaction relating to an address of the smart contract. The transaction can be executed in an EVM of each node, and smart contract code is distributed and run on a virtual machine of each node in the Ethereum network.

In a blockchain using Ethereum as a basic architecture, three MPT trees are designed for data to be stored and maintained in the blockchain, including an MPT state tree, an MPT transaction tree, and an MPT receipt tree. In addition to the three MPT trees, there is actually a storage tree constructed based on storage content of a contract account.

The MPT state tree is an MPT tree including account state data of all accounts in the blockchain, the MPT transaction tree is an MPT tree including transaction data in the blockchain, and the MPT receipt tree is an MPT tree including a transaction receipt that corresponds to each transaction in a block and is generated after the transaction is executed. Hash values of root nodes of the MPT state tree, the MPT transaction tree, and the MPT receipt tree shown above are finally added to a block header of a corresponding block.

Both the MPT transaction tree and the MPT receipt tree correspond to a block, in other words, each block has its own MPT transaction tree and MPT receipt tree. The MPT state tree is a global MPT tree, and does not correspond to a specific block, but covers the account state data of all the accounts in the blockchain.

The MPT transaction tree, the MPT receipt tree, and the MPT state tree are finally stored in a key-value database (e.g., LevelDB) using a multi-level data storage structure.

Generally, there are three types of blockchain networks: a public blockchain, a private blockchain, and a consortium blockchain. In addition, there can be combinations of the above multiple types, such as a combination of a private blockchain and a consortium blockchain, and a combination of a consortium blockchain and a public blockchain.

The public blockchain has the highest degree of decentralization. Bitcoin and Ethereum are representatives of the public blockchain. Participants of the public blockchain (which can also be referred to as nodes in the blockchain) can read data records in the blockchain, participate in transactions, compete for mining rights of new blocks, etc. In addition, each node can freely join or exit a network and perform a related operation.

On the other hand, write permission of the private blockchain network is controlled by a certain organization or agency, and data read permission is specified by the organization. Briefly, the private blockchain can be a weakly centralized system, a strict restriction is imposed on participating nodes, and there are a few participating nodes. This type of blockchain is more suitable for use within a specified organization.

The consortium blockchain is a blockchain between the public blockchain and the private blockchain, and can implement "partial decentralization." Each node in the consortium blockchain usually has a corresponding organization. Participants join the network through authorization and form an interest-related consortium to jointly maintain running of the blockchain.

It can be expected that the implementations provided in the present specification can be implemented in any suitable type of blockchain network.

The client in the one or more implementations provided in the present specification can be an independent device connected to any node device in a blockchain network, or can be a function module disposed inside any node device, which is not limited herein.

Figure 4:
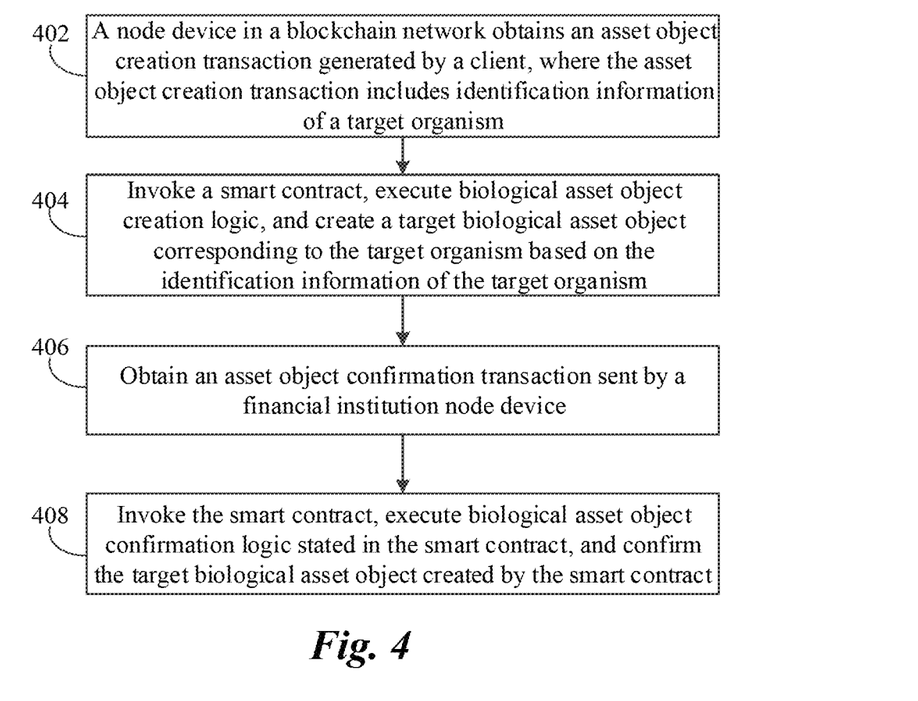
FIG. 4 is a schematic flowchart illustrating a blockchain-based method for managing a biological asset object according to an example implementation.

FIG. 4 shows a blockchain-based method for managing a biological asset object according to an example implementation. A smart contract for managing a biological asset object is deployed in a blockchain, processing logic corresponding to contract code of the smart contract includes biological asset object creation logic, and the method is performed by any node device in the blockchain network, and includes the following steps.

Step 402: Obtain an asset object creation transaction generated by a client, where the asset object creation transaction includes identification information of a target organism.

The identification information of the target organism includes identity attribute information of the target organism that helps to determine an identity of the target organism. For example, the identification information includes a unique identifier, which can uniquely determine the target organism, allocated to the target organism by a biological management agency, and can further include information such as a biological species, a sex, a birth date, a place of origin, and a breeding ground.

Currently, identities of organisms are identified by using ear tags of the organisms. For example, identification information (e.g., one or more of the unique identifier, the species, the sex, the birth date, the place of origin, and the breeding ground described above) of organisms such as cattle and sheep is integrated into ear tags mounted on exposed positions such as ears of the organisms. However, the ear tags are easy to be lost, maliciously replaced, or counterfeited and reused, which easily causes a problem that an identity of an organism is difficult to determine or an identity of an organism is counterfeited, affecting management or use of a biological asset.

The client can obtain the identification information of the target organism by receiving information that is manually input. In another implementation provided in the present specification, the target organism is implanted with a sensing module storing the identification information (including the above identity attribute information) of the target organism, for example, a radio frequency module that can be implanted into the organism. A semiconductor chip, an antenna, and an information transmitting apparatus are integrated into the sensing module. Through perception communication between a sensing module perception device and the module, the identification information of the target organism stored in the sensing module can be received. The client in the above implementation is connected to the sensing module perception device, and obtains the identification information of the target organism by receiving the identification information of the target organism that is sent by the sensing module perception device and obtained by perceiving the sensing module.

In an illustrative implementation, the identification information of the target organism can further include biological characteristic information such as iris characteristic information or genetic material characteristic information (a DNA sequence) of the target organism. Because the biological characteristic information can uniquely correspond to an organism, a problem that an identity of the organism is counterfeited due to operations such as ear tag replacement or counterfeiting can be avoided.

The biological characteristic information can be integrated into an ear tag of the target organism or stored in the sensing module implemented into the organism, to uniquely identify the target organism.

In an illustrative implementation, the client can be connected to a biological feature recognition device. In addition to obtaining the identity attribute information such as the identifier, the biological species, the place of origin, the breeding ground, and the birth date information of the target organism by communicating with the sensing module perception device, through connection to the biological feature recognition device, the client can directly receive the biological characteristic information of the target organism that is collected by the biological feature recognition device and obtained by recognizing the target organism. Compared with integrating the biological characteristic information of the target organism into the sensing module, the blockchain client directly collects the biological characteristic information of the target organism by using the biological feature recognition device before storing the identification information of the target organism in the blockchain, to further prevent the biological characteristic information from being counterfeited and further accurately anchor the target organism.

An iris is a ring-shaped portion between the black pupil and the white sclera on the surface of an eye of an organism, and includes many intertwined detail features such as speckles, filaments, coronas, stripes, and crypts. An iris recognition device can scan an iris of the target organism, and pack an iris feature of the target organism into the iris characteristic information of the target organism based on an iris feature template. It can be determined whether a biological object is the target organism by collecting an iris feature of the biological object, generating iris characteristic information of the biological object, and comparing the iris characteristic information of the biological object with the iris characteristic information of the target organism. Currently, iris recognition has higher recognition accuracy than a biological feature recognition method such as fingerprint recognition, and is easier to operate than a DNA sequence comparison recognition method. Therefore, the iris recognition technology is more applicable to farm animals. In an illustrative implementation, the biological characteristic information of the target organism is the iris characteristic information; and the blockchain client obtains the iris characteristic information of the target organism from the iris recognition device through connection to the iris recognition device.

Step 404: Invoke the smart contract, execute the biological asset object creation logic, and create a target biological asset object corresponding to the target organism based on the identification information of the target organism.

A process of storing the asset object creation transaction in the blockchain can include the following steps:

The client sends the asset object creation transaction constructed by the client to the node device connected to the client, so that the node device broadcasts the asset object creation transaction in the blockchain network; a node with mining rights, e.g., a mining node, in the blockchain can add the asset object creation transaction to a candidate block after receiving the asset object creation transaction; the mining node broadcasts the candidate block to nodes in the blockchain; after the candidate block is verified by a determined quantity of consensus nodes, e.g., a predetermined or quantity of nodes, in the blockchain, the candidate block is considered as the latest block of the blockchain; each node device in the blockchain network adds the latest block to a ledger database of the blockchain after receiving the latest block, and executes a transaction included in the latest block to update, in a state database of the blockchain, a data state corresponding to the transaction included in the latest block.

In the above implementation, the node with mining rights is a node that has permission to generate a candidate block. Based on a consensus mechanism of the blockchain, a consensus node can be determined from nodes with mining rights for the candidate block. The consensus mechanism can include a POW mechanism, a POS mechanism, a DPOS mechanism, a PBFT consensus mechanism, etc., and is not limited herein.

After obtaining the agreed asset object creation transaction, the node device in the blockchain network can execute the smart contract triggered in the asset object creation transaction in an EVM, and create the target biological asset object corresponding to the target organism based on the identification information of the target organism.

The target biological asset object is digital information generated based on the identification information of the target organism, so that an asset of the target organism is digitalized. When the identification information includes unique identification information such as a biological feature, the asset object generated based on the identification information also includes unique digital information. By converting an organism in the real world into a virtual asset in the blockchain, the organism is "anchored" to a biological asset object in the blockchain, and the organism supports value of the biological asset object, to generate asset value matching the organism in the blockchain.

The algorithm, which is stated in the smart contract, of generating the target biological asset object based on the identification information of the target organism is not limited in this implementation. For example, based on algorithm programs stated in the smart contract, hash calculation can be performed on the identification information of the target organism, and mathematical transformation can be further performed on a calculated hash digest, to obtain string information of a predetermined character quantity or a predetermined data format. The string information can be used as the target biological asset object in this implementation.

In an illustrative implementation, based on the smart contract, the target biological asset object can be further created as a structure in the key-value form. The content of the key part of the asset object includes the unique digital information, for example, the string information generated through hash calculation or further mathematical transformation in the above implementation, generated based on the identification information of the target organism. The string information used as the content of the key part can be considered as an address of the biological asset object. The content of the value part can include the identification information of the target organism. As such, a correspondence between the identification information of the target organism and the target biological asset object is established.

The target biological asset object created by the smart contract based on the above implementation can be stored in the state database of the blockchain. In practice, an object type supported by the blockchain can be extended, that is, an asset object is extended based on the object type supported by the blockchain. For example, an asset object can be extended based on an external object and a contract object (or referred to as an external account and a contract account) supported by Ethereum. As such, a physical asset in the real world is used as a value support to create a virtual asset object that can be circulated in the blockchain, for example, the biological asset object described in the present specification.

For a user accessing such a blockchain, in addition to creating a user account and a smart contract in the blockchain, the user can create a virtual asset object that matches the value of a physical asset without a currency attribute in the real world in the blockchain, to be circulated in the blockchain.

For example, the user can convert physical assets held without a currency attribute, such as real estates, stocks, loan contracts, bills, accounts receivable, and biological assets, into value-matched virtual asset objects to be circulated in the blockchain. Content included in a structure of the virtual asset object can be the same as the content included in the structure of the account in Ethereum, or certainly can be designed based on an actual demand.

In an implementation, for example, the content included in the structure of the biological asset object is the same as the content in the structure of the account in Ethereum. The structure of the biological asset object can also include fields such as BALANCE, NONCE, CODE, and STORAGE.

It should be noted that in Ethereum, the BALANCE field is usually used to maintain a current account balance of an account. However, for a blockchain project derived from the Ethereum architecture, because the blockchain project may not support conversion of a currency in the real world into a virtual coin that can be circulated in the blockchain, in such a blockchain, the meaning of the BALANCE field can be extended, so that the BALANCE field no longer represents the "balance" of the account, but is used to maintain address information of an asset object corresponding to a biological asset held by the account. In practice, the BALANCE field can maintain address information of asset accounts corresponding to a plurality of biological assets.

In this case, the external object, the contract object, and the asset object supported by the blockchain all can hold a virtual asset by adding address information of an asset object corresponding to the biological asset object or another virtual asset object to the BALANCE field. In other words, in addition to the external object and the contract object, the asset object itself can also hold a virtual asset.

For the biological asset object, field values of the NONCE field and the CODE field can be null (or may not be null), a field value of the STORAGE field may not be null anymore, and the STORAGE field can be used to maintain an asset state of a "biological asset" corresponding to the biological asset object, for example, the identification information of the organism in the above implementation. Certainly, a specific method for maintaining the asset state corresponding to the asset object in the STORAGE field can be flexibly designed based on a demand, and details are omitted for simplicity.

In an illustrative implementation, in a blockchain project derived from the Ethereum architecture, the user can use the following implementations to create a biological asset object in the blockchain that matches the value of an organism in the real world.

In an implementation, a transaction type supported by the blockchain can be extended to obtain a transaction for creating a biological asset object. For example, transaction types supported by Ethereum usually include a common transfer transaction, a transaction for creating a smart contract, and a transaction for invoking a smart contract. In this case, the three types of transactions can be extended to obtain a transaction for creating a biological asset object.

In this case, the user can publish a transaction for creating a biological asset object in the blockchain network by using the client, and the node device in the blockchain network executes the transaction in a local EVM to create a biological asset object for the user. After an agreement is reached among node devices through a consensus mechanism, the biological asset object is successfully created, and a biological asset object corresponding to the organism appears in the blockchain and has a specified address.

In another implementation, a smart contract for creating a biological asset object can also be deployed in the blockchain, and details of the process of deploying the smart contract for creating a biological asset object are omitted for simplicity.

In this case, the user can publish a transaction for invoking the smart contract in the blockchain network by using the client, and the node device in the blockchain network executes the transaction in a local EVM, and runs contract code related to the smart contract in the EVM, to create a biological asset object for the user. After an agreement is reached among node devices through a consensus mechanism, the biological asset object is successfully created, and a biological asset object corresponding to the organism appears in the blockchain and has a specified address.

In an illustrative implementation, in a process of creating the biological asset object, the biological asset object can be directly stored in a blockchain external object such as a blockchain user account held by a user, to indicate that the biological asset object is held by the user. In this case, the asset object creation transaction sent by the user by using the client can further include a blockchain account identifier of the user who holds the target organism. The process of executing the biological asset object creation logic by the smart contract further includes: storing the target biological asset object in a blockchain user account corresponding to the account identifier, to facilitate management processes such as transaction and circulation of biological asset objects between different blockchain user accounts.

According to the blockchain-based method for managing a biological asset object in the one or more implementations herein, the target biological asset object can be created in the blockchain based on the identification information of the target organism. Based on a blockchain tamper-resistant mechanism, the target biological asset object is anchored to the target organism, so that not only asset information of the target organism is digitized in the blockchain, but also it is convenient to manage the target biological asset object in the blockchain. For example, in breeding, transportation, and transaction processes of the target organism, the source of the asset information of the target organism in the blockchain is traced or traceable, identity information of the target organism is recognized or checked, or management, such as transaction, of the target biological asset object is implemented. For example, the transaction, transportation or other management of the target organism can be monitored and traced through the biological asset object in the blockchain based on the identification information of the target organism.

In the above one or more implementations, through biological feature recognition or implantation of the sensing module that includes the identification information into the organism, the biological asset object stored in the blockchain can be uniquely anchored to the organism, to effectively prevent theft or counterfeiting of the identity of the organism and further ensure the accuracy of information about the biological asset object stored in the blockchain.

When the target organism is used as a biological asset to perform an asset-related financial operation, for example, performing mortgaging on the target organism, or performing a securitization operation on an asset attribute of the target organism and performing transaction and circulation on a securitized biological asset, a financial institution usually needs to determine the asset attribute of the target organism.

Therefore, in an illustrative implementation, the blockchain further includes a financial institution node device. After the target biological asset object is created in the blockchain based on the identification information of the target organism through the process of managing a biological asset object provided in steps 402 to 404 in FIG. 4, the financial institution node device can further obtain the target biological asset object from the database of the blockchain, and confirms the target biological asset object in the blockchain after a service system of the financial institution reviews the information about the target biological asset object. For example, the service system of the financial institution may review the value of the target biological asset object based on all the information of the target organism contained in the block.

In an illustrative implementation, in response to the asset object creation transaction sent by the client, the node device in the blockchain network invokes the smart contract, executes the biological asset object creation logic, and creates the target biological asset object corresponding to the target organism based on the identification information.

The financial institution can learn the target biological asset object that includes the identification information by monitoring the state database of the blockchain locally stored in the node device. After determining that the information about the target biological asset object is correct, the financial institution can send an asset confirmation transaction to the blockchain, so that the node device in the blockchain network obtains the asset confirmation transaction, as described in step 406, and the node device invokes the smart contract, executes biological asset confirmation logic stated in the smart contract, and confirms the target biological asset object created by the smart contract, as shown in step 408. The asset confirmation transaction can include a confirmation indication of the target biological asset object, for example, "Confirmed" or "Authenticated," and the confirmation indication information can be stored in the STORAGE field of the biological asset object structure, so that the target organism can be used as a valid asset and applied to a related financial field, for example, mortgaging or asset securitization.

The smart contract can further perform permission management on a user confirming the biological asset object, so that only a user (e.g., the above financial institution) who has confirmation permission can confirm the biological asset object.

After the financial institution confirms the target biological asset object stored in the blockchain, the form of a valid digitized asset corresponding to the target organism can be created in the blockchain. The tamper-resistant mechanism of the blockchain provides an authoritative guarantee for the financial institution to confirm the target biological asset object, so that the user can use the target organism in the form of the valid asset for related financial activities.

Corresponding to the above procedure implementation, an implementation of the present specification further provides a blockchain-based apparatus 50 for managing biological asset information. The apparatus 50 can be implemented by software, hardware, or a combination of hardware and software. Software implementation is used as an example. As a logical apparatus, the apparatus 50 is formed by reading a corresponding computer program instruction in a memory and running the instruction by a central processing unit (CPU) in a device where the apparatus 50 is located. In terms of hardware implementation, in addition to a CPU, a memory, and a storage shown in FIG. 6, the device where the apparatus is located generally further includes other hardware such as a chip for sending and receiving radio signals, and/or other hardware such as a card configured to implement a network communication function.

Figure 5:
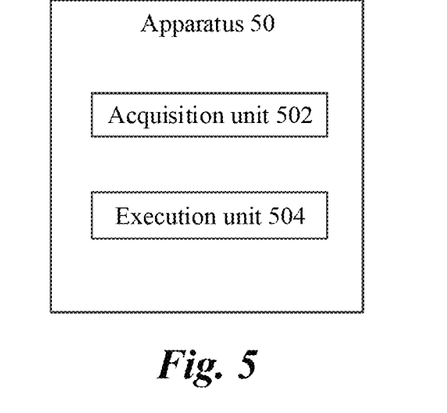
FIG. 5 is a schematic diagram illustrating a blockchain-based apparatus for managing a biological asset object that is applied to a node device in a blockchain network according to an example implementation.

As shown in FIG. 5, the present specification further provides a blockchain-based apparatus 50 for managing a biological asset object. The apparatus is applied to a node device in a blockchain network, a smart contract for managing a biological asset object is deployed in the blockchain, processing logic corresponding to contract code of the smart contract includes biological asset object creation logic, and the apparatus 50 includes: an acquisition unit 502, configured to obtain an asset object creation transaction generated by a client, where the asset object creation transaction includes identification information of a target organism; and an execution unit 504, configured to invoke the smart contract, execute the biological asset object creation logic, and create a target biological asset object corresponding to the target organism based on the identification information of the target organism.

In an illustrative implementation, the target biological asset object includes a unique identifier generated based on the identification information of the target organism.

In an illustrative implementation, the asset object creation transaction further includes an account identifier of a blockchain user who holds the biological asset object, and the executing the biological asset object creation logic further includes: storing the target biological asset object in a blockchain user account corresponding to the account identifier.

In an illustrative implementation, the identification information of the target organism includes one or more of identity attribute information collected from sensing hardware mounted on the target organism or biological characteristic information of the target organism collected from the target organism.

In an illustrative implementation, the identity attribute information includes one or more of an identity number, a biological species, a place of origin, a breeding ground, and birth date information. In an illustrative implementation, the biological characteristic information includes iris characteristic information or genetic material characteristic information. For a specific implementation process of functions of the units in the apparatus 50, references can be made to an implementation process of corresponding steps in the blockchain-based method for managing a biological asset object that is performed by the node device. For related parts, references can be made to descriptions in the method implementation. Details are omitted herein for simplicity.

The above apparatus implementation is merely an example. The units described as separate parts may or may not be physically separate, and parts displayed as units may or may not be physical modules, and may be located in one position, or may be distributed on a plurality of network modules. Some or all of the units or modules can be selected based on actual requirements to achieve the objectives of the solutions of the present specification. A person of ordinary skill in the art can understand and implement the implementations of the present specification without making innovative efforts.

The apparatuses, units, or modules described in the above implementations can be implemented by a computer chip or an entity, or can be implemented by a product with a certain function. A typical implementation device is a computer, and the computer can be specifically a personal computer, a laptop computer, a cellular phone, a camera phone, a smartphone, a personal digital assistant, a media player, a navigation device, an email receiving and sending device, a game console, a tablet, a wearable device, or any combination of these devices.

Figure 6:
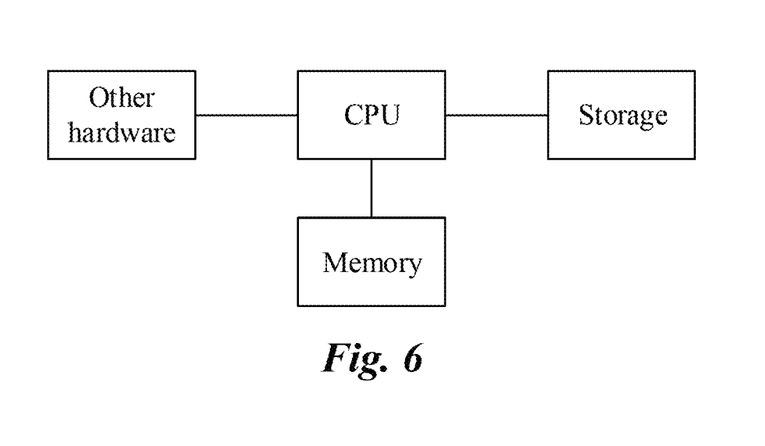
FIG. 6 is a structural diagram illustrating hardware running an implementation of the apparatus for managing a biological asset object provided in the present specification.

Corresponding to the above method implementation, an implementation of the present specification further provides a computer device. As shown in FIG. 6, the computer device includes a storage and a processor. The storage stores a computer program that can be run by the processor. When running the stored computer program, the processor performs the steps of the blockchain-based method for managing a biological asset object that is performed by the node device in the implementations of the present specification. For a detailed description of the steps in the blockchain-based method for managing a biological asset object that is performed by the node device, references can be made to the above content. Details are omitted for simplicity.

Corresponding to the above method implementation, an implementation of the present specification further provides a computer-readable storage medium. The storage medium stores a computer program. When running the computer program, a processor performs the steps in the blockchain-based method for managing a biological asset object that is performed by the node device in the implementations of the present specification. For a detailed description of the steps in the blockchain-based method for managing a biological asset object that is performed by the node device, references can be made to the above content. Details are omitted for simplicity.

The above descriptions are merely preferred implementations of the present specification, but are not intended to limit the present specification. Any modification, equivalent replacement, or improvement made without departing from the spirit and principle of the present specification shall fall within the protection scope of the present specification.

To provide further context for embodiments of this specification, and as introduced herein, distributed ledger systems (DLSs) (which can also be referred to as consensus networks, made up of peer-to-peer nodes), and blockchain networks, enable participating entities to securely, and immutably, conduct transactions and store data. Although the term blockchain is generally associated with particular networks, and/or use cases, blockchain is used herein to generally refer to a DLS without reference to any particular use case.

A blockchain is a data structure that stores transactions in a way that the transactions are immutable. Thus, the recording of transactions on a blockchain is reliable and trustworthy. A blockchain includes one or more blocks. Each block in the chain is linked to a previous block immediately before it in the chain by including a cryptographic hash of the previous block. Each block also includes a timestamp, its own cryptographic hash, and one or more transactions. Within a block, the transactions, which have already been verified by the nodes of the blockchain network, are hashed and encoded into a Merkle tree. The Merkle tree is a data structure in which each leaf node includes a hash on a corresponding transaction, and each non-leaf node includes a hash on the concatenation of the hashes in its children. With this process continuing up the tree to the root of the entire tree, the root node includes a hash that is representative of all data in the tree. A hash purporting to be of a transaction stored in the tree can be quickly verified by determining whether it is consistent with the structure of the tree.

Where a blockchain is a decentralized or at least partially decentralized data structure for storing transactions, a blockchain network is a network of computing nodes that manage, update, and maintain one or more blockchains by broadcasting, verifying and validating transactions, etc. As introduced above, a blockchain network can be provided as a public blockchain network, a private blockchain network, or a consortium blockchain network. Embodiments of this specification are described in further detail herein with reference to a consortium blockchain network. However, embodiments of this specification can be realized in any appropriate type of blockchain network.

In general, a consortium blockchain network is private among the participating entities. In a consortium blockchain network, the consensus process is controlled by an authorized set of nodes, referred to as consensus nodes, one or more of which are operated by a respective entity (a financial institution, insurance company, etc.). For example, a consortium of ten (10) entities (financial institutions, insurance companies, etc.) can operate a consortium blockchain network, each of which operates at least one node in the consortium blockchain network.

In some examples, within a consortium blockchain network, a global blockchain is provided as a blockchain that is replicated across all nodes. That is, all consensus nodes are typically in perfect state consensus with respect to the global blockchain. To achieve consensus (agreement to the addition of a block to a blockchain), a consensus protocol or algorithm is implemented within the consortium blockchain network. For example, the consortium blockchain network can implement a practical Byzantine fault tolerance (PBFT) consensus, described in further detail below.

Figure 7:
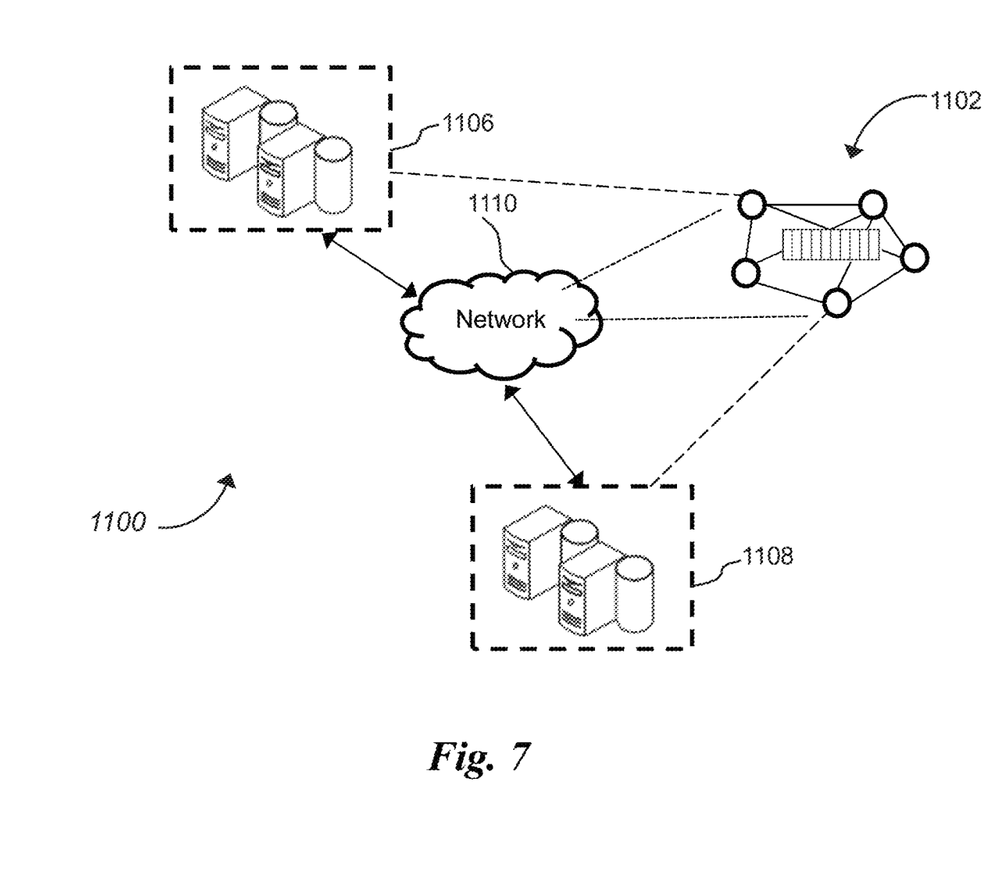
FIG. 7 is a diagram illustrating example environments that can be used to execute embodiments of this specification.

FIG. 7 is a diagram illustrating an example of an environment 1100 that can be used to execute embodiments of this specification. In some examples, the environment 1100 enables entities to participate in a consortium blockchain network 1102. The environment 1100 includes a plurality of computing devices 1106, 1108, and a network 1110. In some examples, the network 1110 includes a local area network (LAN), wide area network (WAN), the Internet, or a combination thereof, and connects web sites, user devices (computing devices), and back-end systems. In some examples, the network 1110 can be accessed over a wired and/or a wireless communications link. In some examples, the network 1110 enables communication with, and within the consortium blockchain network 1102. In general the network 1110 represents one or more communication networks. In some cases, the network 1110 includes network hardware such as switches, routers, repeaters, electrical cables and optical fibers, light emitters and receivers, radio transmitters and receivers, and the like. In some cases, the computing devices 1106, 1108 can be nodes of a cloud computing system (not shown), or each computing device 1106, 1108 can be a separate cloud computing system including a number of computers interconnected by a network and functioning as a distributed processing system.

In the depicted example, the computing systems 1106, 1108 can each include any appropriate computing system that enables participation as a node in the consortium blockchain network 1102. Examples of computing devices include, without limitation, a server, a desktop computer, a laptop computer, a tablet computing device, and a smartphone. In some examples, the computing systems 1106, 1108 host one or more computer-implemented services for interacting with the consortium blockchain network 1102. For example, the computing system 1106 can host computer-implemented services of a first entity (user A), such as a transaction management system that the first entity uses to manage its transactions with one or more other entities (other users). The computing system 1108 can host computer-implemented services of a second entity (user B), such as a transaction management system that the second entity uses to manage its transactions with one or more other entities (other users). In the example of FIG. 7, the consortium blockchain network 1102 is represented as a peer-to-peer network of nodes, and the computing systems 1106, 1108 provide nodes of the first entity and second entity, respectively, which participate in the consortium blockchain network 1102.

Figure 8:
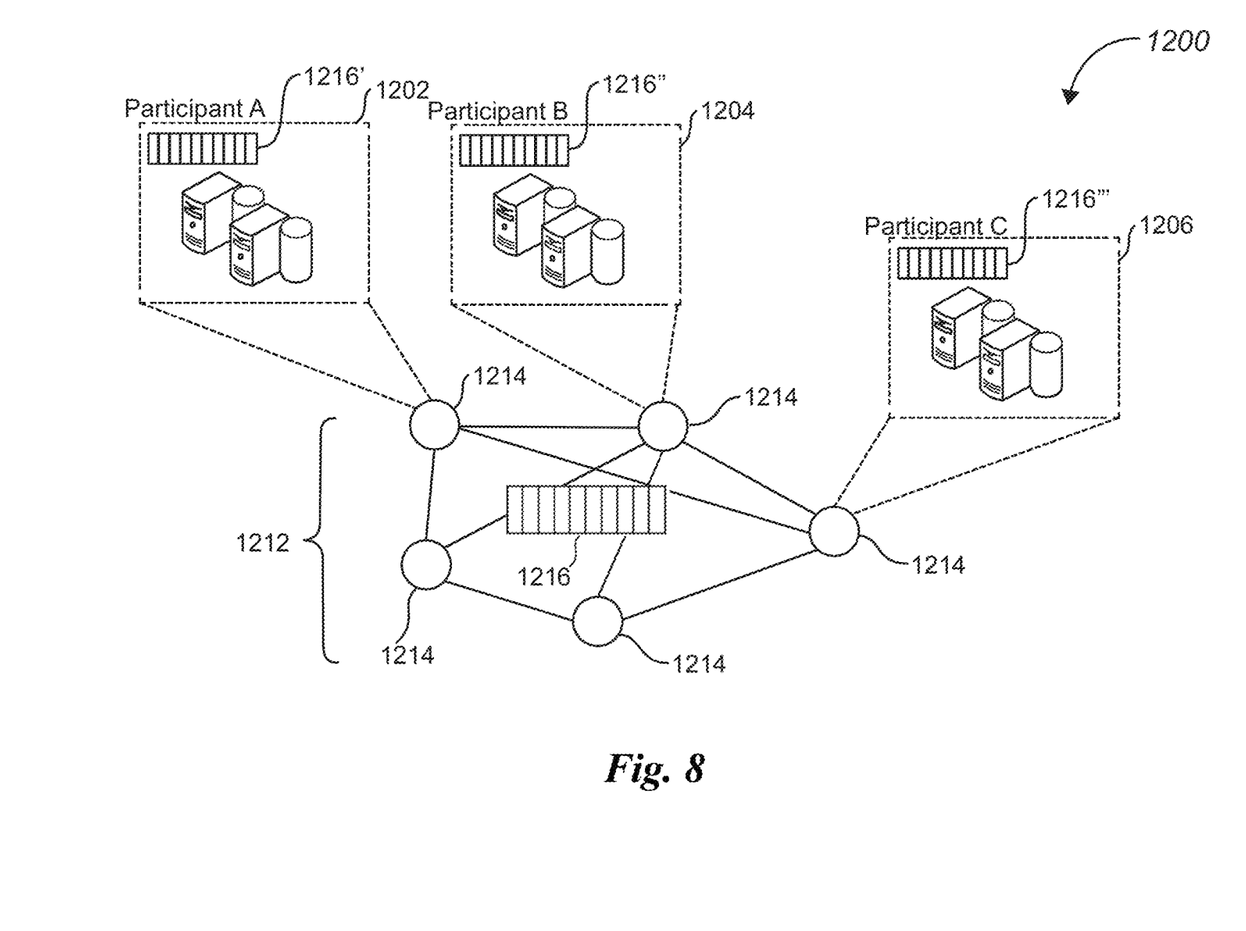
FIG. 8 is a diagram illustrating an example architecture in accordance with embodiments of this specification.

FIG. 8 depicts an example architecture 1200 in accordance with embodiments of this specification. The example architecture 1200 includes participant systems 1202, 1204, 1206 that correspond to Participant A, Participant B, and Participant C, respectively. Each participant (user, enterprise, etc.) participates in a blockchain network 1212 provided as a peer-to-peer network including a plurality of nodes 1214, at least some of which immutably record information in a blockchain 1216. Although a single blockchain 1216 is schematically depicted within the blockchain network 1212, multiple copies of the blockchain 1216 are provided, and are maintained across the blockchain network 1212, as described in further detail herein.

In the depicted example, each participant system 1202, 1204, 1206 is provided by, or on behalf of, Participant A, Participant B, and Participant C, respectively, and functions as a respective node 1214 within the blockchain network 1212. As used herein, a node generally refers to an individual system (computer, server, etc.) that is connected to the blockchain network 1212, and enables a respective participant to participate in the blockchain network. In the example of FIG. 8, a participant corresponds to each node 1214. It is contemplated, however, that a participant can operate multiple nodes 1214 within the blockchain network 1212, and/or multiple participants can share a node 1214. In some examples, the participant systems 1202, 1204, 1206 communicate with, or through, the blockchain network 1212 using a protocol (hypertext transfer protocol secure (HTTPS)), and/or using remote procedure calls (RPCs).

Nodes 1214 can have varying degrees of participation within the blockchain network 1212. For example, some nodes 1214 can participate in the consensus process (as miner nodes that add blocks to the blockchain 1216), while other nodes 1214 do not participate in the consensus process. As another example, some nodes 1214 store a complete copy of the blockchain 1216, while other nodes 1214 only store copies of portions of the blockchain 1216. For example, data access privileges can limit the blockchain data that a respective participant stores within its respective system. In the example of FIG. 8, the participant systems 1202, 1204 store respective, complete copies 1216', 1216", 1216''' of the blockchain 1216. In the descriptions herein, nodes 1214 of the blockchain network 1212 are also referred to as "participant user" for descriptive purposes. In some embodiments, some or all of the participant users 1214 participate in the consensus process and are referred to as "consensus nodes." The consensus nodes for the blockchain 1216 may also include other nodes not selected from the participant users 1214. In some other embodiments, consensus nodes for adding blocks to the blockchain 1216 do not overlap with the participant users 1214 that propose blocks to be added to the blockchain 1216.

A blockchain, such as the blockchain 1216 of FIG. 8, is made up of a chain of blocks, each block storing data. Examples of data include transaction data representative of a transaction between two or more participants. While transactions are used herein by way of non-limiting example, any appropriate data can be stored in a blockchain (documents, images, video, audio, etc.). Examples of a transaction can include, without limitation, exchanges of something of value (assets, products, services, currency, etc.) or occurrence of some events or activities. The transaction data is immutably stored within the blockchain. That is, an undetectable change cannot be made to the transaction data.

Before being stored in a block, the transaction data is hashed. Hashing is a process of transforming the transaction data, typically provided as string data, into a fixed-length hash value, typically provided as string data. It is not possible to un-hash the hash value to obtain the transaction data. Hashing ensures that even a slight change in the transaction data results in a completely different hash value. Further, and as noted above, the hash value is of a fixed length. That is, no matter the size of the transaction data the length of the hash value is fixed. Hashing includes processing the transaction data through a hash function to generate the hash value. An example of a hash function includes, without limitation, the secure hash algorithm (SHA)-256, which outputs 256-bit hash values.

Transaction data of multiple transactions are hashed and stored in a block. For example, hash values of two transactions are provided, and are themselves hashed to provide another hash. This process is repeated until, for all transactions to be stored in a block, a single hash value is provided. This hash value is referred to as a Merkle root hash, and is stored in a header of the block. A change in any of the transactions will result in change in its hash value, and ultimately, a change in the Merkle root hash.

Blocks are added to the blockchain through a consensus protocol. Multiple nodes within the blockchain network participate in the consensus protocol, and perform work to have a block added to the blockchain. Such nodes are referred to as consensus nodes. PBFT, introduced above, is used as a non-limiting example of a consensus protocol. The consensus nodes execute the consensus protocol to add transactions to the blockchain, and update the overall state of the blockchain network.

In further detail, for example, the consensus node generates a block header, hashes all of the transactions in the block, and combines the hash value in pairs to generate further hash values until a single hash value is provided for all transactions in the block (the Merkle root hash). This Merkle root hash is added to the block header. The consensus node also determines the hash value of the most recent block in the blockchain (the last block added to the blockchain) and adds the hash value of the most recent block into the block header. The consensus node also adds a nonce value, and a timestamp to the block header. The block header is hashed, which becomes the hash value of the block.

In general, PBFT provides a practical Byzantine state machine replication that tolerates Byzantine faults (malfunctioning nodes, malicious nodes, etc.). This is achieved in PBFT by assuming that faults will occur (assuming the existence of independent node failures, and/or manipulated messages sent by consensus nodes). In PBFT, the consensus nodes are provided in a sequence that includes a primary consensus node and backup consensus nodes. The primary consensus node is periodically changed. Transactions are added to the blockchain by all consensus nodes within the blockchain network reaching an agreement as to the world state of the blockchain network. In this process, messages are transmitted between consensus nodes, and each consensus nodes proves that a message is received from a specified peer node and verifies that the message was not modified during transmission.

In PBFT, the consensus protocol is provided in multiple phases with all consensus nodes beginning in the same state. To begin, a client sends a request to the primary consensus node to invoke a service operation (execute a transaction within the blockchain network). In response to receiving the request, the primary consensus node multicasts the request to the backup consensus nodes. The backup consensus nodes execute the request, and each sends a reply to the client. The client waits until a threshold number of replies are received. In some examples, the client waits for f+1 replies to be received, where f is the maximum number of faulty consensus nodes that can be tolerated within the blockchain network. The final result is that a sufficient number of consensus nodes come to an agreement on the order of the record that is to be added to the blockchain, and the record is either accepted, or rejected.

A consensus algorithm refers to a specific mechanism or terms, based on which a transaction or a block is verified and validated to be added into a blockchain. To that extent, a consensus algorithm is viewed as a specific implementation agreement adapted to follow rules of a consensus protocol. Different consensus algorithms may be created for different blockchain networks 1212 or different blockchains 1216, which all comply with a same consensus protocol.

In some blockchain networks, cryptography is implemented to maintain privacy of transactions. For example, if two nodes want to keep a transaction private, such that other nodes in the blockchain network cannot discern details of the transaction, the nodes can encrypt the transaction data. An example of cryptography includes, without limitation, symmetric encryption and asymmetric encryption. Symmetric encryption refers to an encryption process that uses a single key for both encryption (generating ciphertext from plaintext), and decryption (generating plaintext from ciphertext). In symmetric encryption, the same key is available to multiple nodes, so each node can encrypt/decrypt transaction data.

Asymmetric encryption uses keys pairs that each include a private key, and a public key, the private key being known only to a respective node, and the public key being known to any or all other nodes in the blockchain network. A node can use the public key of another node to encrypt data, and the encrypted data can be decrypted using other node's private key. For example, and referring again to FIG. 8, Participant A can use Participant B's public key to encrypt data, and send the encrypted data to Participant B. Participant B can use its private key to decrypt the encrypted data (ciphertext) and extract the original data (plaintext). Messages encrypted with a node's public key can only be decrypted using the node's private key.

Asymmetric encryption is used to provide digital signatures, which enables participants in a transaction to confirm other participants in the transaction, as well as the validity of the transaction. For example, a node can digitally sign a message, and another node can confirm that the message was sent by the node based on the digital signature of Participant A. Digital signatures can also be used to ensure that messages are not tampered with in transit. For example, and again referencing FIG. 8, Participant A is to send a message to Participant B. Participant A generates a hash of the message, and then, using its private key, encrypts the hash to provide a digital signature as the encrypted hash. Participant A appends the digital signature to the message, and sends the message with digital signature to Participant B. Participant B decrypts the digital signature using the public key of Participant A, and extracts the hash. Participant B hashes the message and compares the hashes. If the hashes are same, Participant B can confirm that the message was indeed from Participant A, and was not tampered with.

In a typical configuration, a computing device includes one or more processors (CPU), an input/output interface, a network interface, and a memory.

The memory can include a non-persistent memory, a random access memory (RAM), a non-volatile memory, and/or another form that are in a computer-readable medium, for example, a read-only memory (ROM) or a flash random access memory (flash RAM). The memory is an example of the computer-readable medium.

The computer-readable medium includes persistent, non-persistent, movable, and unmovable media that can store information by using any method or technology. The information can be a computer-readable instruction, a data structure, a program module, or other data.

Examples of a computer storage medium include but are not limited to a phase-change random access memory (PRAM), a static random access memory (SRAM), a dynamic random access memory (DRAM), another type of random access memory (RAM), a read-only memory (ROM), an electrically erasable programmable read-only memory (EEPROM), a flash memory or another memory technology, a compact disc read-only memory (CD-ROM), a digital versatile disc (DVD) or another optical storage, a cassette magnetic tape, a magnetic tape/magnetic disk storage or another magnetic storage device. The computer storage medium can be used to store information accessible by the computing device. Based on the definition in the present specification, the computer-readable medium does not include transitory computer readable media (transitory media) such as a modulated data signal and carrier.

It should be further noted that the terms "include," "comprise," or their any other variants are intended to cover a non-exclusive inclusion, so a process, a method, a product or a device that includes a list of elements not only includes those elements but also includes other elements which are not expressly listed, or further includes elements inherent to such process, method, product or device. Without more constraints, an element preceded by "includes a . . . " does not preclude the existence of additional identical elements in the process, method, product or device that includes the element.

A person skilled in the art should understand that an implementation of the present specification can be provided as a method, a system, or a computer program product. Therefore, the implementations of the present specification can use a form of hardware only implementations, software only implementations, or implementations with a combination of software and hardware. Moreover, the present specification can use a form of a computer program product that is implemented on one or more computer-usable storage media (including but not limited to a disk memory, a CD-ROM, an optical memory, etc.) that include computer-usable program code.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A blockchain-based method for managing a biological asset object, the method comprising:
generating, by a blockchain agent associated to a blockchain node of a blockchain network, biological feature information of a target organism through sensing a biological feature of the target organism via a biological feature recognition device coupled to the blockchain agent;
obtaining an asset object creation transaction, the asset object creation transaction including the biological feature information of the target organism;
invoking a smart contract deployed in the blockchain network, the smart contract including a biological asset object creation logic;
executing the biological asset object creation logic;
creating a target biological asset object corresponding to the target organism based on the biological feature information of the target organism; and
storing the target biological asset object in a blockchain of the blockchain network.

2. The method according to claim 1, wherein the target biological asset object includes a unique identifier generated based on the biological feature information of the target organism.

3. The method according to claim 1, wherein the asset object creation transaction further includes an account identifier of a user who holds the target biological asset object, and the storing the target biological asset object in the blockchain of the blockchain network includes:
storing the target biological asset object in a blockchain user account corresponding to the account identifier of the user.

4. The method according to claim 1, wherein the asset object creation transaction includes identity attribute information collected from sensing hardware mounted on the target organism.

5. The method according to claim 4, wherein the identity attribute information includes one or more of an identity number, a biological species, a place of origin, a breeding ground, and birth date information.

6. The method according to claim 1, wherein the biological feature information includes iris characteristic information or genetic material characteristic information.

7. A blockchain-based apparatus for managing a biological asset object, the apparatus comprising:
a blockchain agent configured to generate biological feature information of a target organism through sensing a biological feature of the target organism via a biological feature recognition device coupled to the blockchain agent;

an acquisition unit, configured to obtain an asset object creation transaction, the asset object creation transaction including the biological feature information of a target organism; and an execution unit, configured to invoke a smart contract deployed in a blockchain network, execute a biological asset object creation logic of the smart contract, create a target biological asset object corresponding to the target organism based on the biological feature information of the target organism, and store the target biological asset object in a blockchain of the blockchain network.

8. The apparatus according to claim 7, wherein the target biological asset object includes a unique identifier generated based on the biological feature information of the target organism.

9. The apparatus according to claim 7, wherein the asset object creation transaction further includes an account identifier of a blockchain user who holds the target biological asset object, and the storing the target biological asset object in the blockchain of the blockchain network includes:

storing the target biological asset object in a blockchain user account corresponding to the account identifier of the user.

10. The apparatus according to claim 7, wherein the asset object creation transaction includes identity attribute information collected from sensing hardware mounted on the target organism.

11. The apparatus according to claim 10, wherein the identity attribute information includes one or more of an identity number, a biological species, a place of origin, a breeding ground, and birth date information.

12. The apparatus according to claim 4-07, wherein the biological feature information includes iris characteristic information or genetic material characteristic information.

13. A computer device, comprising a storage and a processor, the storage storing a computer program that can be run by the processor, and when running the computer program, the processor performing acts including:

generating, by a blockchain agent associated to a blockchain node of a blockchain network, biological feature information of a target organism through sensing a biological feature of the target organism via a biological feature recognition device coupled to the blockchain agent;

obtaining an asset object creation transaction, the asset object creation transaction including the biological feature information of the target organism;

invoking a smart contract deployed in a blockchain network, the smart contract including a biological asset object creation logic;

executing the biological asset object creation logic;

creating a target biological asset object corresponding to the target organism based on the biological feature information of the target organism; and storing the target biological asset object in a blockchain of the blockchain network.

14. The computer device according to claim 13, wherein the target biological asset object includes a unique identifier generated based on the biological feature information of the target organism.

15. The computer device according to claim 13, wherein the asset object creation transaction includes an account identifier of a user who holds the target biological asset object, and the storing the target biological asset object in the blockchain of the blockchain network includes:

storing the target biological asset object in a blockchain user account corresponding to the account identifier of the user.

16. The computer device according to claim 13, wherein the asset object creation transaction includes identity attribute information collected from sensing hardware mounted on the target organism.

17. The computer device according to claim 16, wherein the identity attribute information includes one or more of an identity number, a biological species, a place of origin, a breeding ground, and birth date information.

18. The computer device according to claim 13, wherein the biological feature information includes iris characteristic information or genetic material characteristic information.

19. The computer device according to claim 13, wherein the acts include validating the target biological asset object.

20. The computer device according to claim 19, wherein the validating the target biological asset object includes determining an attribute of the target biological asset object.

* * * * *

UNITED STATES PATENT AND TRADEMARK OFFICE
CERTIFICATE OF CORRECTION

Page 1 of 1

PATENT NO. : 11,710,129 B2
APPLICATION NO. : 17/353525
DATED : July 25, 2023
INVENTOR(S) : Yingqiang Wu It is certified that error appears in the above-identified patent and that said Letters Patent is hereby corrected as shown below:

In the Claims

Column 21, Claim 12, Line 34:
"according to claim 4-07, wherein" should read: --according to claim 7, wherein--.

Signed and Sealed this
Eleventh Day of March, 2025

Coke Morgan Stewart
*Acting Director of the United States Patent and Trademark Office*